US009549702B1

(12) United States Patent
Kerness et al.

(10) Patent No.: US 9,549,702 B1
(45) Date of Patent: Jan. 24, 2017

(54) SYSTEM INCLUDING INTEGRATED OPTICAL SENSORS FOR DETERMINATION OF IMPAIRMENT OF MOTORIZED SYSTEM OPERATORS

(71) Applicant: Maxim Integrated Products, Inc., San Jose, CA (US)

(72) Inventors: Nicole D. Kerness, Menlo Park, CA (US); Joy T. Jones, Fremont, CA (US); Arvin Emadi, Santa Clara, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 62 days.

(21) Appl. No.: 14/565,812

(22) Filed: Dec. 10, 2014

Related U.S. Application Data

(60) Provisional application No. 62/018,058, filed on Jun. 27, 2014.

(51) Int. Cl.
| | |
|---|---|
| *A61B 5/1455* | (2006.01) |
| *A61B 5/18* | (2006.01) |
| *A61B 5/00* | (2006.01) |
| *A61B 5/024* | (2006.01) |
| *B60W 50/00* | (2006.01) |

(52) U.S. Cl.
CPC ............ *A61B 5/18* (2013.01); *A61B 5/0064* (2013.01); *A61B 5/02427* (2013.01); *A61B 5/1455* (2013.01); *B60W 50/00* (2013.01)

(58) Field of Classification Search
None
See application file for complete search history.

(56) References Cited

U.S. PATENT DOCUMENTS

| | | | | |
|---|---|---|---|---|
| 5,907,407 A | * | 5/1999 | Atkinson | ............... G01N 21/39 356/326 |
| 6,167,746 B1 | * | 1/2001 | Gammenthaler | .... B60K 28/063 180/272 |
| 7,299,890 B2 | * | 11/2007 | Mobley | ............... B60K 28/063 180/272 |

(Continued)

OTHER PUBLICATIONS

Pending U.S. Appl. No. 14/497,654, filed Sep. 26, 2014 titled Nondispersive Infrared Micro-Optics Sensor for Blood Alcohol Concentration Measurements.

*Primary Examiner* — Jonathan M Dager
(74) *Attorney, Agent, or Firm* — Advent LLP

(57) ABSTRACT

A system includes one or more optical sensors for the measuring and monitoring of physiological information of a motorized system operator. The system is configured to determine an incapacitation state of the motorized system operator based upon the measured physiological information. When the measured physiological information indicates an incapacitation state (intoxication level, stress level, and so forth), the system is configured to provide a response thereto including, but not limited to: lock out operation of the motorized system, provide a warning on a display, transmit a message from the motorized system, assume automatic control of the motorized system, and so forth. The system includes a plurality of light sources (e.g., light-emitting diodes (LEDs)), one or more photodetectors, and control circuitry coupled to the plurality of light sources and/or photodetectors to non-invasively measure physiological information (e.g., blood alcohol concentration, stress levels, and so forth).

20 Claims, 2 Drawing Sheets

(56) References Cited

U.S. PATENT DOCUMENTS

| | | | |
|---|---|---|---|
| 2002/0089660 A1* | 7/2002 | Weiss | A61B 5/18 356/72 |
| 2005/0230175 A1* | 10/2005 | Brown | B60K 28/063 180/272 |
| 2008/0183388 A1* | 7/2008 | Goodrich | A61B 5/14546 701/300 |
| 2009/0087920 A1* | 4/2009 | Pettersson | B60K 28/066 436/132 |
| 2010/0036592 A1* | 2/2010 | Osaki | B60T 7/14 701/113 |
| 2010/0125187 A1* | 5/2010 | Osaki | A61B 5/14546 600/322 |
| 2011/0127101 A1* | 6/2011 | Johnson | A61B 3/112 180/272 |
| 2012/0031166 A1* | 2/2012 | Lopez | G01N 33/4972 73/23.3 |
| 2012/0188532 A1* | 7/2012 | Li | B60K 28/06 356/51 |
| 2015/0038123 A1* | 2/2015 | Tuukkanen | H04W 4/16 455/414.1 |
| 2015/0094914 A1* | 4/2015 | Abreu | B60H 1/00742 701/41 |

* cited by examiner

SYSTEM INCLUDING INTEGRATED OPTICAL SENSORS FOR DETERMINATION OF IMPAIRMENT OF MOTORIZED SYSTEM OPERATORS

CROSS-REFERENCE TO RELATED APPLICATIONS

The present application claims the benefit under 35 U.S.C. §119(e) of U.S. Provisional Application Ser. No. 62/018,058, entitled SYSTEM INCLUDING INTEGRATED OPTICAL SENSORS FOR DETERMINATION OF IMPAIRMENT OF MOTORIZED SYSTEM OPERATORS, filed Jun. 27, 2014. U.S. Provisional Application Ser. No. 62/018,058 is hereby incorporated by reference in its entirety.

BACKGROUND

Electronic devices, such as smart phones, tablet computers, digital media players, and so forth, increasingly employ light sensors to control the manipulation of a variety of functions provided by the device. For example, light sensors are commonly used by electronic devices to detect ambient lighting conditions in order to control the brightness of the device's display screen. Light sensors often employ photodetectors such as photodiodes, phototransistors, or the like, which convert received light into an electrical signal (e.g., a current or voltage). Electronic devices can also include light sensors for communicating information. For example, devices can employ pulse oximeters, which use light to detect a person's pulse and blood oxygen levels, in order to display the person's physiological information on the display screen of the device.

SUMMARY

A system is described that includes one or more optical sensors for the measuring and monitoring of physiological information of a motorized system operator. The system is configured to determine an incapacitation state (intoxication level, stress level, and so forth) of the motorized system operator based upon the measured physiological information. When the measured physiological information indicates an incapacitation state, the system is configured to provide a response thereto including, but not limited to: lock out operation of the motorized vehicle, provide a warning on a display, transmit a message from the vehicle, assume automatic control of the vehicle, and so forth. The system includes a plurality of light sources (e.g., light-emitting diodes (LEDs)), one or more photodetectors, and control circuitry coupled to the plurality of light sources and/or photodetectors to non-invasively measure physiological information (e.g., blood alcohol concentration, stress levels, and so forth).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

An individual's ability to operate a motorized system is based in part on the individual's physical and mental capabilities, and can be inhibited by various incapacitating events. Motorized systems can include motorized vehicles (e.g., car, truck, train, bus, plane, helicopter, motorcycle, ship, boat, watercraft, and so forth) and motorized equipment (e.g., construction equipment, fabrication equipment, loading equipment, and so forth). When an operator of the motorized system becomes incapacitated in some manner, the safe operation of the motorized system can be jeopardized. Certain chemical substances (e.g., alcohol, tetrahydrocannabinol (THC), controlled substances, and so forth) and mental/physical states (e.g., stress levels, acute health risk, and so forth) can influence the individual's ability to safely operate the motorized system. For example, when alcohol is ingested, the alcohol is absorbed into the body's bloodstream and distributed throughout the body via the circulatory system, where the alcohol can be subsequently metabolized by or excreted from the body. A measure of blood alcohol concentration or content (BAC) can provide a metric for an individual's level of intoxication, where higher measurements typically project a higher level of physical/mental impairment or incapacitation as compared to lower measurements.

Methods for measuring physiological conditions, such as blood alcohol concentration, can involve an ex vivo analysis of a bodily fluid, such as through an ex vivo analysis of expelled gas (e.g., breath analysis), blood, urine, and saliva. Such analysis of bodily fluids can be undesirable for efficiency, privacy, or other reasons. Other methods for measuring physiological conditions can involve bulky equipment that is not configured for integration in mobile devices or mobile motorized systems, and would not provide an indication of an individual's impairment or incapacity level at the time of use of a motorized system.

Accordingly, a system is described that includes one or more optical sensors for the measuring and monitoring of physiological information of a motorized system operator. The system is configured to determine an incapacitation state of the motorized system operator based upon the measured physiological information. When the measured physiological information indicates an incapacitation state, the system is configured to provide a response thereto including, but not limited to: lock out operation of the motorized system, provide a warning on a display, transmit a message from the motorized system, assume automatic control of the motorized system, and so forth. The system includes a plurality of light sources (e.g., light-emitting diodes (LEDs)), one or more photodetectors, and control circuitry coupled to the plurality of light sources and/or photodetectors to non-invasively measure physiological information (e.g., blood alcohol concentration, stress levels, and so forth).

Example Implementations

Figure 1A:
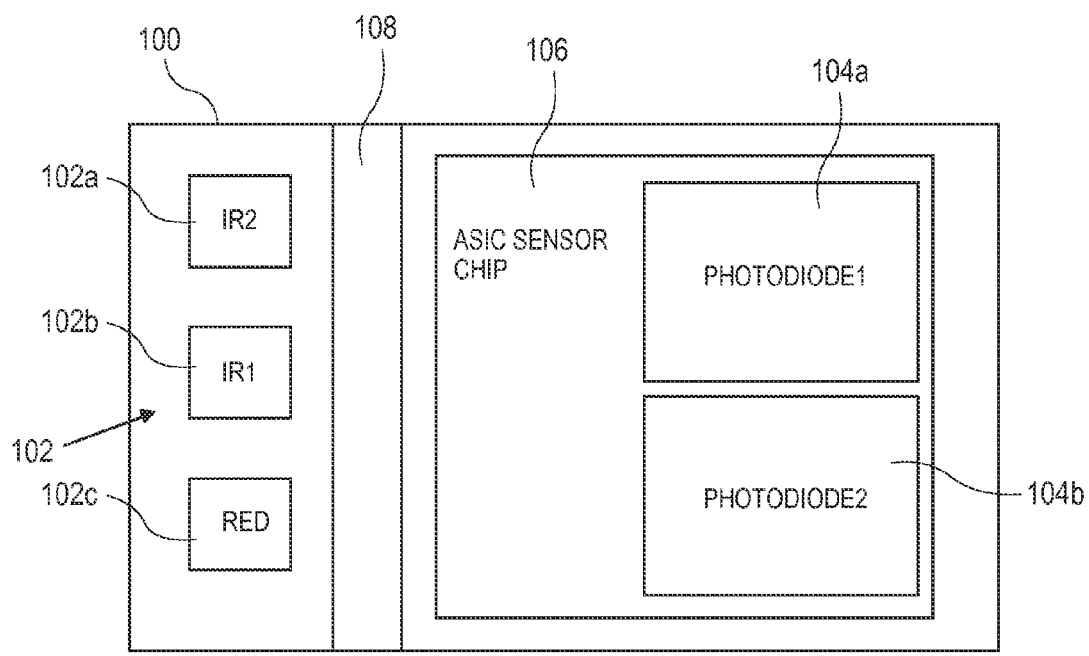
FIG. 1A is a diagrammatic side view illustrating an optics-based sensor for the measurement of one or more physiological conditions in accordance with example implementations of the present disclosure.
Figure 1B:
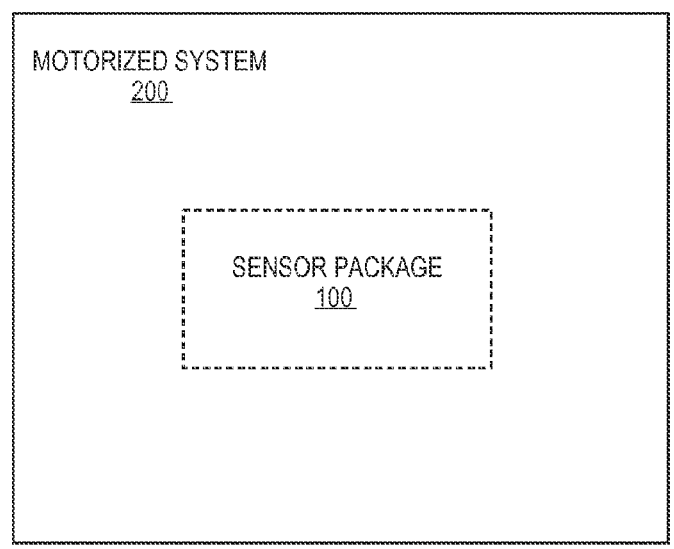
FIG. 1B is a schematic illustration of a motorized system including the optics-based sensor of FIG. 1A.

Referring to FIG. 1A, a sensor package 100 for the measurement of one or more physiological conditions is shown in accordance with example implementations of the present disclosure. In embodiments, such as shown in FIG. 1B, the sensor package 100 is integrated with a motorized system 200, which can include a motorized vehicle (e.g., car, truck, train, bus, plane, helicopter, motorcycle, ship, boat, watercraft, and so forth) and motorized equipment (e.g., construction equipment, fabrication equipment, loading equipment, and so forth). As shown, the sensor package 100 includes a plurality of light sources 102 (light sources 102a, 102b, and 102c are shown), one or more photodetectors 104 (photodetectors 104a and 104b are shown), and an application specific integrated circuit (ASIC) sensor chip 106 operably coupled to the plurality of light sources 102 and the photodetector 104. A baffle 108 is shown positioned between the plurality of light sources 102 and the photodetector 104 to provide an obstruction against direct cross-contamination of light from the plurality of light sources 102 directly to the photodetector 104. In general operation, light from the plurality of light sources 102 is directed to a user proximate the sensor package 100. The light is scattered, absorbed, and reflected throughout the user, where the photodetector 104 measures light leaving the user. The ASIC sensor chip 106 includes control circuitry configured to drive the plurality of light sources 102, to read/receive the output from the photodetector 104, and to process the received signal, such as through signal conditioning, whereby a digital output (e.g., of a physiological condition, such as blood alcohol concentration within the user) can be provided from the sensor package 100. In implementations, the sensor package 100 is configured as a non-dispersive micro-optics sensor for blood alcohol concentration measurements, such as described in U.S. application Ser. No. 14/497,654, entitled NONDISPERSIVE INFRARED MICRO-OPTICS SENSOR FOR BLOOD ALCOHOL CONCENTRATION MEASUREMENTS, filed Sep. 26, 2014, which is hereby incorporated by reference in its entirety. In implementations, the sensor package 100 includes an optical interferometer for the detection of alcohol and other compounds in the user's blood. In various implementations, the output from the sensor package 100 is analyzed to determine whether a measured physiological condition is indicative of a physical or mental impairment of the user, whereby an action is taken with respect to operation of the motorized system 200. The analysis can be performed by a processing component of the motorized system 200, by a component of the sensor package 100, by a processing component of another system, and so forth. The action taken with respect to operation of the motorized system 200 can involve a lockout of operation of the motorized system 200, thereby preventing the user from operating the motorized system 200 while impaired (such as while intoxicated), can involve display of a warning of potential impairment on a display screen on/proximate to the motorized system, can involve transmission of a message from the motorized system, can involve assumption of automatic control of the motorized system, and so forth.

In implementations, the plurality of light sources 102 share a lens (not shown) configured to direct the light from the light sources 102 into user, although the light sources 102 can utilize individualized lens for one or more of the light sources 102. The lens can include a downward curvature, an upward curvature, no curvature (e.g., a plain "window" configuration), and so forth. The lens can be configured to condition (e.g., block, filter, focus, collimate, diffuse, etc.) electromagnetic radiation from the plurality of light sources 102 to the user. The lens can be positioned above one or more reflectors (e.g., parabolic reflectors) configured to reflect light from the plurality of light sources 102 up to the lens. In an alternative implementation, the sensor package 100 includes a metalized interior surface having a parabolic shape to reflect light from the plurality of light sources 102 up to the lens.

In embodiments, the light sources 102 may include one or more light emitting diodes (LED), one or more vertical-cavity surface-emitting lasers (VCSEL), and so forth. The light sources 102 can be present in a single cavity or can be provided in separate cavities on the sensor package 100. In various implementations, each of the plurality of light sources includes a light source configured to produce light in a distinct spectrum or spectra. For example, in one implementation, light source 102a is configured to produce light in a red visible spectrum (e.g., light having an approximately 660 nm wavelength), light source 102b is configured to produce light in an infrared spectrum (e.g., light having an approximately 880 nm wavelength), and light source 102c is configured to produce light in a spectrum from approximately one micron to approximately three microns. In implementations, the 660 nm and 880 nm wavelengths facilitate pulse oximetry measurements, whereas the one to three micron wavelengths facilitate blood alcohol measurements.

The photodetectors 104 are configured to receive and process light received from the plurality of light sources 102. Each photodetector 104 can be configured to process light from one or more of the plurality of light sources 102. For example, one or more photodetectors 104 can be a near-IR sensor, such as a III-V compound photodetector, a thermopile, a bolometer, and so forth configured to detect the output of light scattered from the user. The photodetectors 104 can include photodiodes, phototransistors, or the like. The sensor package 100 can include wavelength filters at a package level or positioned proximate to one or more of the photodetectors 104, such as positioned over one or more of photodetectors 104a and 104b. In an implementation a wavelength filter specific to alcohol measurements is utilized. While FIG. 1A shows photodetectors 104a and 104b on the ASIC sensor chip 106, in other various implementations, the photodetectors 104 are provided on separate chips.

The plurality of lights 102, the photodetectors 104, and the ASIC sensor chip 106 are configured to provide an indication of a physiological condition of a user of the motorized system 200. For example, in implementations, the sensor package 100 is configured to measure or determine one or more of a blood alcohol concentration, a pulse, a heart rate, a blood oxygenation level, a stress level, a tetrahydrocannabinol (THC) level, and so forth, of a user. The sensor package 100 and/or the motorized system can be configured to determine whether the measured physiological condition is indicative of a physical or mental impairment or incapacitation of the user. When the sensor package 100 and/or the motorized system 200 determines (e.g., via a computerized processing device, software, firmware, and the like) that the measured physiological condition is indicative of a physical or mental impairment or incapacitation of the user, the sensor package 100 and/or the motorized system 200 is configured to take an action in response thereto, such as to prevent unsafe operation of the motorized system 200. For example, the action taken can involve a lockout of operation of the motorized system 200, thereby preventing the user from operating the motorized system 200 while impaired (such as while intoxicated, under the influence of a drug, having a high stress level). In implementations, the sensor package 100 includes a body portion that is coupled with a component of the motorized system 200, such as a steering wheel, a start button, a key fob, a button on an external surface of the motorized system (e.g., a button to unlock the motorized system 200, open a door of the motorized system 200, etc.), and so forth. In implementations, the sensor package 100 includes a communications interface configured to transmit one or more communication signals to a switching element configured to perform the action responsive to the determination of impairment, such as by locking out operation of the motorized system 200 responsive to reception of the communication signals. The communication signals can include, but are not limited to, wired communication signals and wireless communication signals, such as acoustic communication signals, optical communication signals, radio communication signals, infrared communication signals, ultrasonic communication signals, and the like.

Other actions can involve display of a warning of potential impairment on a display screen on/proximate to the motorized system, such as to warn the user or others proximate the user of a potentially unsafe motorized system operation. For instance, where the user has legitimate need to operate the motorized system while under stress (e.g., driving a passenger to an emergency room, etc.), the system can warn the user, but still allow operation of the motorized system 200. Other actions can involve transmission of a message from the motorized system 200, such as a message transmitted to a remote entity for the purpose of seeking assistance for the user. For example, the sensor package 100 and/or the motorized system 200 could transmit a message to a taxi service requesting transportation assistance for an impaired driver. Other actions can involve assumption of automatic control of the motorized system, such as by having a motorized vehicle assume automatic control of the vehicle to take the user to a particular destination.

In implementations, the sensor package 100 includes or is operably coupled with a finger print sensor. For example, the finger print sensor can be utilized to identify an individual whose physiological conditions are being monitored or measured. The sensor package 100 can generate signals associated with the physiological conditions, which can be stored in a memory device, such as to create a record of the particular individual, their physiological conditions while operating the motorized system 200, their history of stressful operation of the motorized system, and so forth. The memory is an example of tangible computer-readable media that provides storage functionality to store various data associated with operation of device controllers, such as software programs and/or code segments, or other data to instruct a processor and possibly other components of the controller to perform the steps described herein. A wide variety of types and combinations of memory may be employed. The memory may be integral with the processor, may comprise stand-alone memory, or may be a combination of both. The memory may include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, and so forth. In embodiments, the controller and/or memory may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

Example Processes

Figure 2:
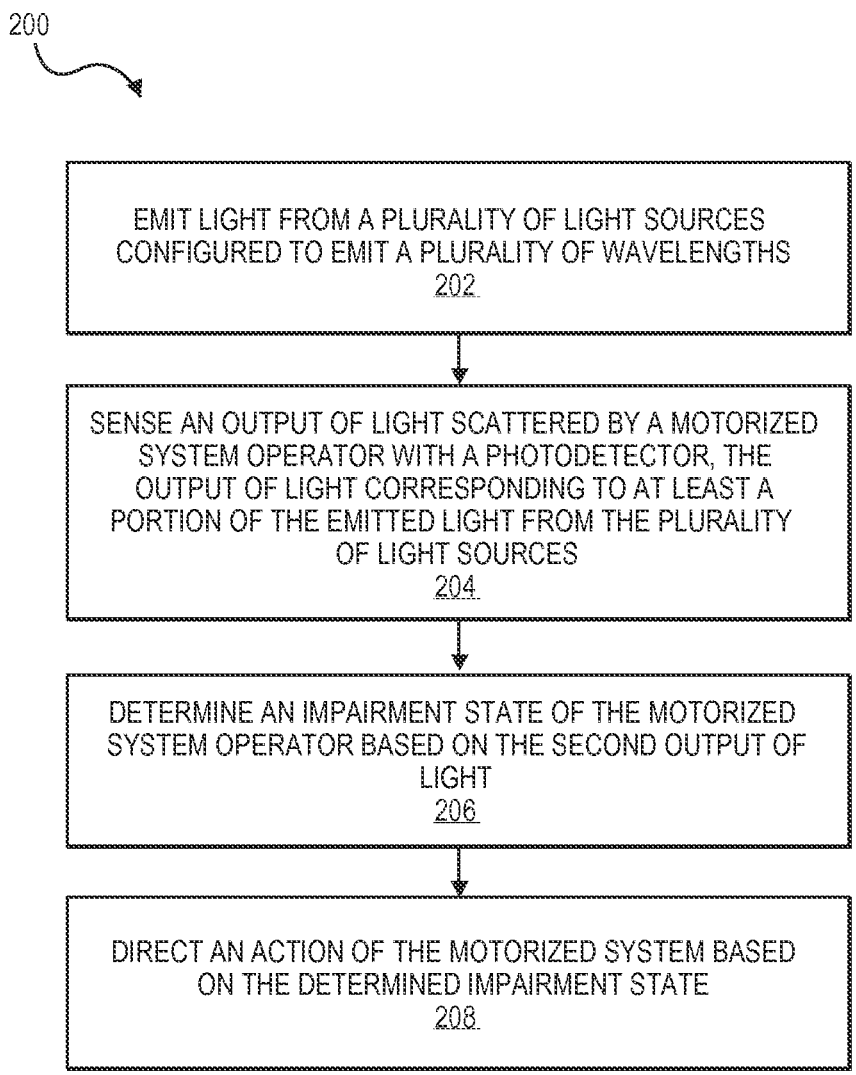
FIG. 2 is a flow diagram illustrating a process in an example implementation for utilizing an optics-based sensor for the measurement of one or more physiological conditions, such as the sensor shown in FIGS. 1A and 1B.

FIG. 2 provides a flow diagram illustrating a process 200 in an example implementation for utilizing an optics-based sensor for the measurement of physiological conditions, such as the sensor package 100 shown in FIGS. 1A and 1B. As shown, process 200 includes emitting light from a plurality of light sources configured to emit a plurality of wavelengths (Block 202). For example, the plurality of light sources 102 can be configured to emit light having a plurality of different wavelengths (e.g., light sources 102a, 102b, 102c) toward an operator of a motorized system.

Process 200 also includes sensing an output of light scattered from a motorized system operator with a photodetector, where the output of light corresponds to at least a portion of the emitted light from the plurality of light sources (Block 204). For example, the photodetectors 104 are configured to sense an output of light scattered from a motorized system operator, where the scattered light corresponds to at least a portion of light from the plurality of light sources 102, such as light that was emitted, but not absorbed by the operator's body.

Process 200 also includes determining an impairment state of the motorized system operator based on the sensed output of light (Block 206). For example, the sensor package 100 can be configured to measure or determine one or more of a blood alcohol concentration, a pulse, a heart rate, a blood oxygenation level, a stress level, a tetrahydrocannabinol (THC) level, and so forth based upon the sensed output of light by the photodetectors 104. The sensor package 100 and/or the motorized system 200 can be configured to determine whether the measured physiological condition is indicative of a physical or mental impairment or incapacitation of the user, such as by comparison of the measured physiological condition to reference data indicative of a physical or mental impairment or incapacitation. For instance, the sensor package 100 and/or the motorized system 200 can compare the output from the sensors of the sensor package 100 to reference data indicative of a physical or mental impairment or incapacitation, which can include, but is not limited to, blood alcohol concentrations and associated impairments, pulse rates corresponding to stress levels, and so forth.

Process 200 further includes directing an action of the motorized system based on the determined impairment state (Block 208). For example, the sensor package 100 and/or the motorized system 200 is configured to determine (e.g., via a computerized processing device, software, firmware, and the like) that the measured physiological condition is indicative of a physical or mental impairment or incapacitation of the user, the sensor package 100 and/or the motorized system 200 is configured to take an action in response thereto, such as to prevent unsafe operation of the motorized system 200. In various implementations, the action taken involves a lockout of operation of the motorized system 200, thereby preventing the user from operating the motorized system 200 while impaired (such as while intoxicated, under the influence of a drug, having a high stress level, etc.).

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A sensor package for physiological measurements and responses thereto, comprising:
   a plurality of light sources configured to emit a plurality of wavelengths, the plurality of light sources including a first light source configured to emit light having a first spectrum of wavelengths to detect a first physiological condition of a user and a second light source configured to emit light having a second spectrum of wavelengths to detect a second physiological condition of the user;
   at least one photodetector; and
   an application specific integrated circuit coupled to the plurality of light sources and the at least one photodetector, the application specific integrated circuit configured to detect and calibrate signal outputs from the at least one photodetector to determine an impairment state of the user based on the first physiological condition of the user and the second physiological condition of the user.

2. The sensor package as recited in claim 1, wherein the application specific integrated circuit is further configured to direct an action to be taken with respect to operation of a motorized system responsive to determination of the impairment state.

3. The sensor package as recited in claim 2, wherein the action includes a lockout of operation of the motorized system.

4. The sensor package as recited in claim 2, wherein the action includes display of the impairment state.

5. The sensor package as recited in claim 2, wherein the action includes transmission of a message from the motorized system.

6. The sensor package as recited in claim 1, wherein the impairment state corresponds to a blood alcohol concentration.

7. The sensor package as recited in claim 1, wherein the impairment state corresponds to a stress level.

8. The sensor package as recited in claim 1, wherein the impairment state corresponds to a tetrahydrocannabinol concentration.

9. The sensor package as recited in claim 1, wherein the at least one photodetector is configured to detect at least one of a blood alcohol concentration, a heart rate, a pulse, a stress level, and a tetrahydrocannabinol concentration.

10. The sensor package as recited in claim 1, further comprising:
    a body portion operably coupled with one or more of the plurality of light sources, the at least one photodetector, and the application specific integrated circuit, the body portion configured for coupling with a component of a motorized system.

11. The sensor package as recited in claim 10, wherein the component of the motorized system includes one or more of a steering wheel, a start button, a key fob, and a button on an external surface of the motorized system.

12. The sensor package as recited in claim 1, further comprising a finger print sensor.

13. A system configured to measure physiological conditions and respond thereto, comprising:
    a motorized system; and
    a sensor package integrated into the motorized system, the sensor package including:
       a plurality of light sources configured to emit a plurality of wavelengths, the plurality of light sources including a first light source configured to emit light having a first spectrum of wavelengths to detect a first physiological condition of a user and a second light source configured to emit light having a second spectrum of wavelengths to detect a second physiological condition of the user;
       at least one photodetector; and
       an application specific integrated circuit coupled to the plurality of light sources and the at least one photodetector, the application specific integrated circuit configured to detect and calibrate signal outputs from the at least one photodetector to determine an impairment state of the user based on the first physiological condition of the user and the second physiological condition of the user and to direct an action to be taken with respect to operation of the motorized system.

14. The system as recited in claim 13, wherein the action includes a lockout of operation of the motorized system.

15. The system as recited in claim 13, wherein the action includes display of the impairment state.

16. The system as recited in claim 13, wherein the action includes transmission of a message from the motorized system.

17. The system as recited in claim 13, wherein the action includes assumption of automatic control of the motorized system.

18. A process for determining impairment of a motorized system operator and responding thereto, comprising:
    emitting light from at least a first light source and a second light source, the first light source configured to emit light having a first spectrum of wavelengths to detect a first physiological condition of a user, the second light source configured to emit light having a second spectrum of wavelengths to detect a second physiological condition of the user;
    sensing an output of light scattered from an operator of a motorized system with a photodetector, the output of light corresponding to at least a portion of the emitted light from the first light source and the second light source;
    determining an impairment state of the operator of the motorized system based on the sensed output of light; and
    directing an action of the motorized system based on the determined impairment state.

19. The process as recited in claim 18, wherein the action includes at least one of a lockout of operation of the motorized system, display of the impairment state, transmission of a message from the motorized system, and assumption of automatic control of the motorized system.

20. The sensor package as recited in claim 1, wherein the plurality of light sources further includes a third light source, and wherein the first light source is configured to produce light in a red visible spectrum, the second light source is configured to produce light in an infrared spectrum, and the third light source is configured to produce light in a spectrum from one micron to three microns.

* * * * *